United States Patent
Downer et al.

(10) Patent No.: US 9,781,922 B2
(45) Date of Patent: Oct. 10, 2017

(54) AMINE AND AMINE OXIDE SURFACTANTS FOR CONTROLLING HERBICIDE SPRAY DRIFT

(71) Applicant: Dow AgroSciences LLC, Indianapolis, IN (US)

(72) Inventors: Brandon Matthew Downer, Lebanon, IN (US); Mei Li, Westfield, IN (US); Lei Liu, Carmel, IN (US); Kuide Qin, Chapel Hill, NC (US); Holger Tank, Indianapolis, IN (US); Stephen L. Wilson, Zionsville, IN (US); Hong Zhang, Carmel, IN (US); Jinxia Susan Sun, Hopewell Junction, NY (US); Shawn Zhu, Stormville, NY (US)

(73) Assignee: Dow AgroSciences LLC, Indianapolis, IN (US)

( * ) Notice: Subject to any disclaimer, the term of this patent is extended or adjusted under 35 U.S.C. 154(b) by 444 days.

(21) Appl. No.: 14/191,699

(22) Filed: Feb. 27, 2014

(65) Prior Publication Data
US 2014/0179529 A1   Jun. 26, 2014

Related U.S. Application Data

(62) Division of application No. 13/232,377, filed on Sep. 14, 2011.

(60) Provisional application No. 61/383,074, filed on Sep. 15, 2010.

(51) Int. Cl.
*A01N 25/30* (2006.01)
*A01N 25/24* (2006.01)
*A01N 57/20* (2006.01)
*A01N 37/40* (2006.01)

(52) U.S. Cl.
CPC ............. *A01N 25/24* (2013.01); *A01N 25/30* (2013.01); *A01N 37/40* (2013.01); *A01N 57/20* (2013.01)

(58) Field of Classification Search
CPC .... A01N 25/30; A01N 57/20; A01N 2300/00; A01N 37/40; A01N 39/04; A01N 43/40
USPC .................................................. 504/127, 128
See application file for complete search history.

(56) References Cited

U.S. PATENT DOCUMENTS

| | | |
|---|---|---|
| 5,710,103 A | 1/1998 | Magin et al. |
| 5,998,332 A | 12/1999 | Sato et al. |
| 2005/0261130 A1 | 11/2005 | Lennon et al. |
| 2009/0318294 A1* | 12/2009 | Malec ................... A01N 57/02 504/206 |
| 2011/0190130 A1 | 8/2011 | Carranza Garzon |

FOREIGN PATENT DOCUMENTS

WO   PCT/US11/51535   2/2012

* cited by examiner

*Primary Examiner* — Johann R Richter
*Assistant Examiner* — Courtney Brown
(74) *Attorney, Agent, or Firm* — Michael J. Terapane

(57) ABSTRACT

Spray drift during the application of an aqueous mixture of glyphosate and an auxinic herbicide is reduced by incorporating certain tertiary amine or tertiary amine oxide surfactants into the aqueous solution or mixture to be sprayed.

11 Claims, No Drawings

AMINE AND AMINE OXIDE SURFACTANTS FOR CONTROLLING HERBICIDE SPRAY DRIFT

This application is a divisional application of U.S. patent application Ser. No. 13/232,377 filed Sep. 14, 2011, which claims the benefit of U.S. Provisional Patent Application Ser. No. 61/383,074 filed Sep. 15, 2010.

BACKGROUND

Agricultural spraying by economical and available technologies uses hydraulic spray nozzles that inherently produce a wide spectrum of spray droplet sizes. The potential for these spray droplets to drift from the initial, desired site of application is found to be a function of droplet size, with smaller droplets having a higher propensity for off-target movement. Significant research efforts, involving numerous field trials, wind tunnel tests and subsequent generation of predictive math models have led to a greatly enhanced understanding of the relationship between spray droplet size and potential for off-target drift. Although other factors such as meteorological conditions and spray boom height contribute to the potential for drift, spray droplet size distribution has been found to be a predominant factor. Teske et. al. (Teske M. E., Hewitt A. J., Valcore, D. L. 2004. *The Role of Small Droplets in Classifying Drop Size Distributions* ILASS Americas 17$^{th}$ Annual Conference: Arlington Va.) have reported a value of <156 microns (μm) as the fraction of the spray droplet distribution that contributes to drift. Robert Wolf (Wolf, R. E., *Minimizing Spray Drift*, Dec. 15, 1997, Microsoft® PowerPoint Presentation, available at www.bae.ksu.edu/faculty/wolf/drift.htm, last viewed Sep. 6, 2011) cites a value of <200 μm as the driftable fraction. A good estimation of droplet size likely to contribute to drift, therefore, is the fraction below about 150 μm.

The negative consequences of off-target movement can be quite pronounced. Some herbicides have demonstrated very sensitive phytotoxicity to particular plant species at extremely low parts per million (ppm) or even parts per billion (ppb) levels, resulting in restricted applications around sensitive crops, orchards, and residential plantings. For example, the California Dept of Pesticide Regulation imposes buffers of ½-2 miles for propanil containing herbicides applied aerially in the San Joaquin valley.

SUMMARY

Spray drift during application can be reduced by incorporating certain tertiary amine or tertiary amine oxide surfactants into an aqueous herbicidal spray mixture containing glyphosate and an auxinic herbicide. Methods and compositions to reduce spray drift during the application of an aqueous herbicidal spray mixture are described herein. The methods to reduce spray drift during the application of an aqueous herbicidal spray mixture containing glyphos ate and an auxinic herbicide include incorporating into the aqueous herbicidal spray mixture from about 0.02 to about 2 weight percent of one of a tertiary amine surfactant of the formula:

$$R^1-\underset{\underset{R^2}{|}}{N}-R^3$$

wherein $R^1$ is a straight or branched chain ($C_{12}$-$C_{18}$) alkyl and $R^2$ and $R^3$ independently are straight or branched chain ($C_1$-$C_{18}$) alkyl, or a tertiary amine oxide surfactant of the formula:

$$R^4-\underset{\underset{O^-}{|}}{\overset{\overset{R^5}{|}}{N^+}}-R^6$$

wherein $R^4$ is a straight or branched chain ($C_{10}$-$C_{18}$) alkyl or an alkyletherpropyl or alkylamidopropyl of the formula:

$$R^7-O-\text{\textasciitilde}\quad \text{or} \quad R^7-\underset{\underset{}{}}{\overset{\overset{O}{\|}}{C}}-\underset{H}{N}-\text{\textasciitilde}$$

wherein $R^7$ is a straight or branched chain ($C_{10}$-$C_{18}$) alkyl, and $R^5$ and $R^6$ independently are straight or branched chain ($C_1$-$C_{18}$) alkyl or ethoxylates or propoxylates of the formula:

$$\text{\textasciitilde}[C_2H_4O]_n H \quad \text{or} \quad \text{\textasciitilde}[C_2H_3(CH_3)O]_n H$$

wherein n is an integer from 1 to 20, or mixtures thereof.

Additionally, aqueous concentrate compositions are described that include from about 5 to about 40 weight percent of a water soluble salt of at least one auxinic herbicide, about 5 to about 40 weight percent of a water soluble salt of glyphosate, and from about 1 to about 20 weight percent of one or more tertiary amine or tertiary amine oxide.

DETAILED DESCRIPTION

Methods and compositions to reduce spray drift are described herein. The methods and compositions reduce the amount of driftable fines of a herbicide spray in both aerial and ground spray applications. The methods include the use of compositions incorporating tertiary amine or tertiary amine oxide surfactants, or mixtures thereof, into aqueous herbicidal spray mixtures containing a water soluble glyphosate salt and at least one water soluble auxinic herbicide salt. Particularly useful auxinic herbicides to which this method applies include clopyralid, triclopyr, 2,4-D, 2,4-DB, MCPA, MCPB, dicamba, aminopyralid, and picloram. The methods described herein are most particularly useful for the application of herbicides that are subject to restricted applications around sensitive crops such as spray mixtures containing glyphosate and 2,4-D, triclopyr or dicamba.

Suitable cations contained in the water soluble salt of glyphosate and the water soluble salt of the auxinic herbicide used in the spray mixtures described herein include isopropyl ammonium, dimethyl ammonium, triethyl ammonium, monoethanol ammonium, diethanol ammonium, triethanol ammonium, dimethylethanol ammonium, diethyleneglycol ammonium, triisopropanol ammonium, tetramethyl ammonium, tetraethyl ammonium, and choline.

The tertiary amine and tertiary amine oxide surfactants useful with the methods and compositions described herein may be prepared from petroleum derived raw materials or from naturally derived raw materials such as, for example, vegetable, animal, algae, or seed oils, or from combinations of petroleum derived or naturally derived raw materials.

As used herein tertiary amine surfactants refer to trialkyl amines of the formula $$R^1\diagdown\underset{N}{\overset{R^2}{|}}\diagup R^3$$

wherein $R^1$ is a straight or branched chain ($C_{12}$-$C_{18}$) alkyl and $R^2$ and $R^3$ independently are straight or branched chain ($C_1$-$C_{18}$) alkyls. Examples of useful tertiary amine surfactants include those found in products such as, for example, Armeen® DMTD (cocoalkyldimethylamine; AkzoNobel, Chicago, Ill.) and the like.

As used herein tertiary amine oxide surfactants refer to trialkyl amine oxides of the formula $$R^4\diagdown\underset{\underset{O^-}{|}}{\overset{R^5}{\overset{|}{N_+}}}\diagup R^6$$

wherein $R^4$ is a straight or branched chain ($C_{10}$-$C_{18}$) alkyl or an alkyletherpropyl or alkylamidopropyl of the formula $$R^7\diagdown O\diagdown\diagdown\diagdown \quad \text{or} \quad R^7-\underset{H}{\overset{O}{\overset{||}{C}}}-N\diagdown\diagdown\diagdown$$

wherein $R^7$ is a straight or branched chain ($C_{10}$-$C_{18}$) alkyl, and $R^5$ and $R^6$ independently are straight or branched chain ($C_1$-$C_{18}$) alkyl or ethoxylates or propoxylates of the formula $$\diagdown\diagdown[C_2H_4O]_n\diagdown H \quad \text{or} \quad \diagdown\diagdown[C_2H_3(CH_3)O]_n\diagdown H$$

wherein n is an integer from 1 to 20, or mixtures thereof. Examples of useful tertiary amine oxide surfactants include those found in the following products such as, for example, Ammonyx® C ($R^4$ is cocoalkyl; $R^5$ and $R^6$ are methyl), Ammonyx® MO ($R^4$ is straight chain $C_{14}$ alkyl; $R^5$ and $R^6$ are methyl), Ammonyx® MCO ($R^4$ is indicated to be predominantly a mixture of straight chain $C_{14}$ and $C_{16}$ alkyls; $R^5$ and $R^6$ are methyl), Ammonyx® LO ($R^4$ is straight chain $C_{12}$ alkyl; $R^5$ and $R^6$ are methyl) and Ammonyx® CDO ($R^4$ is cocoamidopropyl; $R^5$ and $R^6$ are methyl) (the Ammonyx® line of products are available from Stepan Company, Northfield, Ill.); Rhodamox® LO ($R^4$ is indicated to be predominantly a mixture of straight chain $C_{12}$ and $C_{14}$ alkyls; $R^5$ and $R^6$ are methyl) (Rhodia-Novecare; Cranbury, N.J.); Aromox® C/12 ($R^4$ is cocoalkyl; $R^5$ and $R^6$ are 2-hydroxethyl) and Aromox® APA-T ($R^4$ is tallowalkylamidopropyl; $R^5$ and $R^6$ are methyl) (the Aromox® line of products are available from AkzoNobel, Chicago, Ill.); and the Tomamine® AO series of surfactants such as, for example, Tomamine® AO-728 ($R^4$ is linear alkyletherpropyl; $R^5$ and $R^6$ are 2-hydroxethyl) (the Tomamine® AO series of surfactants are available from Air Products, Allentown, Pa.).

The tertiary amine or tertiary amine oxide surfactant, and mixtures thereof, can be incorporated into the aqueous herbicidal spray mixture, for example, by being tank-mixed directly with the diluted herbicidal formulation. The tertiary amine or tertiary amine oxide surfactant, and mixtures thereof, may be incorporated into the aqueous spray mixture at a concentration from about 0.02 to about 2 weight percent of the final spray mixture, preferably from about 0.05 to about 1.0 weight percent of the final spray mixture, and most preferably from about 0.05 to about 0.2 weight percent of the final spray mixture.

The optimum spray droplet size depends on the application for which the composition is used. If droplets are too large, there will be less coverage by the spray; i.e, large droplets will land in certain areas while areas in between will receive little or no spray coverage. The maximum acceptable droplet size may depend on the amount of composition being applied per unit area and the need for uniformity in spray coverage. Smaller droplets provide more even coverage, but are more prone to drift during spraying. Thus, application parameters such as uniformity in spray coverage must be balanced against the tendency for smaller droplets to drift. For example, if it is particularly windy during spraying, larger droplets may be needed to reduce drift, whereas on a calmer day smaller droplets may be acceptable.

In addition to the physical properties of a particular aqueous composition, spray droplet size may also depend on the spray apparatus, e.g., nozzle size and configuration. The reduction in spray drift may result from a variety of factors including a reduction in the production of fine spray droplets (<150 μm minimum diameter) and an increase in the volume median diameter (VMD) of the spray droplets. In any event, for a given spray apparatus, application, and conditions, and based on the tertiary amine or tertiary amine oxide surfactant used, the median diameter of the plurality of spray droplets created using the compositions and methods described herein is increased above that of a spray composition that does not include the tertiary amine or tertiary amine oxide surfactants as described herein.

In addition to the methods described above, aqueous concentrate compositions are also described. As used herein aqueous concentrate compositions are solutions containing high concentrations of the aqueous herbicidal spray components described above, i.e., a water soluble glyphosate salt, one or more water soluble auxinic herbicide salts, and one or more tertiary amine or tertiary amine oxide surfactants. The aqueous concentrate compositions are intended to be diluted to provide aqueous herbicidal spray mixtures for use, for example, with the methods described herein. The aqueous concentrate compositions include from about 5 to about 40 weight percent of one or more water soluble salts of an auxinic herbicide, from about 5 to about 40 weight percent of a water soluble salt of glyphosate, and from about 1 to about 20 weight percent of one or more tertiary amine or tertiary amine oxide surfactants. The aqueous concentrate compositions are preferably solutions containing the one or more tertiary amine or tertiary amine oxide surfactant, or mixtures thereof, dissolved or dispersed in the formulation containing the auxinic herbicide and glyphosate. Preferably the aqueous concentrate compositions contain about 10 to about 40 weight percent of the water soluble glyphosate salt; about 10 to about 40 weight percent of the one or more water soluble auxinic herbicide salts; and about 1 to about 18, about 1 to about 16, about 1 to about 14, about 1 to about 12, about 1 to about 10, about 1 to about 9, about 1 to about 8, about 1 to about 7, about 1 to about 6, about 1 to about 5, about 1 to about 4, about 1 to about 3, about 1 to about 2, or about 1 to about 1.5 weight percent of the one or more tertiary amine or tertiary amine oxide surfactants. Most preferably the aqueous concentrate compositions contain about 15 to about 30, about 20 to about 30, or about 25 to about 30 weight percent of the water soluble glyphosate salt; about 15 to about 30, about 20 to about 30, or about 25 to about 30 weight percent of the one or more water soluble auxinic herbicide salts; and about 1 to about 18, about 1 to about 16, about 1 to about 14, about 1 to about 12, about 1 to about 10, about 1 to about 9, about 1 to about 8, about 1 to about 7, about 1 to about 6, about 1 to about 5, about 1 to about 4, about 1 to about 3, about 1 to about 2, or about 1 to about 1.5 weight percent of the one or more tertiary amine or tertiary amine oxide surfactants. The aqueous concentrate compositions can be stored in suitable containers as will be readily recognized by one of skill in the art and can be, for example, solutions, emulsions, or suspensions.

Aqueous solutions, i.e., including both concentrates and spray solutions, containing 2,4-D and glyphosate are prone to incompatibility under certain conditions and concentrations leading to product performance issues and difficulty in using the products, i.e., difficulty with field applications of the products. Incompatibility in concentrate compositions is minimized by the use of very small amounts of 2,4-D, such as less than about 3 wt % ae (acid equivalent) relative to the total composition. High-strength aqueous compositions of certain organo ammonium salts of 2,4-D and glyphosate where the weight ratio (ae basis) of the 2,4-D salt to the glyphosate salt is from about 2.3:1 to about 1:2.3 and the compositions may contain up to or greater than 450 g ae/L of total active ingredients are described in U.S. application Ser, No.12/763,566, which is incorporated herein by reference. These compositions are generally homogeneous and free-flowing at temperatures ranging from 54° C. to about −10° C.

Optionally, the compositions described herein may contain surfactants in addition to the tertiary amine and tertiary amine oxide surfactants mentioned herein. The additional surfactants may be anionic, cationic, or nonionic in character. Examples of typical surfactants include alcohol-alkylene oxide addition products, such as tridecyl alcohol-$C_{16}$ ethoxylate; sorbitol esters, such as sorbitol oleate; quaternary amines, such as lauryl trimethylammonium chloride; ethoxylated amines, such as tallowamine ethoxylated; betaine surfactants, such as cocoamidopropyl betaine; fatty acid amidopropyl dimethylamine surfactants such as cocoamidopropyl dimethylamine; alkylpolyglycoside surfactants; poly-ethylene glycol esters of fatty acids, such as polyethylene glycol stearate; block copolymers of ethylene oxide and propylene oxide; salts of mono and dialkyl phosphate esters; and mixtures thereof. The additional surfactant or mixture of surfactants is usually present at a concentration of from about 0.5 to about 20 weight percent of the formulation.

Additionally, compositions optionally containing one or more additional compatible ingredients are provided herein. These additional ingredients may include, for example, one or more pesticides or other ingredients, which may be dissolved or dispersed in the composition and may be selected from acaricides, bactericides, fungicides, insecticides, herbicides, herbicide safeners, insect attractants, insect repellents, plant activators, plant growth regulators, and synergists. Also, any other additional ingredients providing functional utility such as, for example, dyes, stabilizers, fragrants, viscosity-lowering additives, compatibility agents, and freeze-point depressants may be included in these compositions.

The following Examples are presented to illustrate various aspects of the compositions and methods described herein and should not be construed as limitations to the claims.

EXAMPLES

Example 1

Herbicide Spray Samples

Herbicide concentrates containing 228 grams acid equivalent per liter (g ae/L) 2,4-D choline, 240 g ae/L glyphosate dimethyl ammonium (DMA), 60 g/L propylene glycol, and 36 g/L (dry weight basis) of the indicated tertiary amine oxide surfactants were prepared as described below using the following aqueous samples of the amine oxide surfactants:

1. Ammonyx® C, 30% w/w cocoalkyldimethylamine oxide in water
2. Ammonyx® MO, 30% weight/weight (w/w) myristyldimethylamine oxide in water
3. Ammonyx® MCO, 30% w/w ($C_{14}$ and $C_{16}$) linear alkyldimethylamine oxide in water
4. Ammonyx® LO, 30% w/w lauryldimethylamine oxide in water
5. Rhodamox® LO, 30% w/w ($C_{12}$ and $C_{14}$) linear alkyldimethylamine oxide in water
6. Aromox® C/12, 50% w/w dihydroxyethyl cocoalkylamine oxide in water
7. Ammonyx® DO, 30% w/w decyldimethylamine oxide in water

[Ammonyx® products are available from Stepan Company (Northfield, Ill.); Rhodamox® products are available from Rhodia-Novecare (Cranbury, N.J.); and Aromox® C/12 is available from AkzoNobel (Chicago, Ill.).]

A 50 milliliter (mL) volumetric flask was first charged with 23.58 g of a 48.35 wt % ae of a 2,4-D choline salt solution in water. To the volumetric flask, 3.00 g of propylene glycol was added and the liquids were then blended by hand shaking the flask until the contents were homogenous. Next, 24.52 g of a 48.95 wt % ae of a glyphosate DMA solution in water was added to the flask. The volumetric flask was once again hand shaken until the contents were blended and homogenous. Next, the tertiary amine oxide surfactant was added (3.60 g of Aromox® C/12 solution; 6.00 g for all others) and the flask was hand shaken until the contents were blended and homogenous. Lastly, deionized water was added to fill the volumetric flask to the 50 mL mark. The sample was then blended by shaking the solution by hand until the liquid was homogenous. Seven samples containing one each of the tertiary amine oxide surfactants listed above and one concentrate containing no tertiary amine oxide surfactant (i.e., control sample) were prepared in this manner.

Each of the herbicide concentrates were then diluted in water to make a 2.49% v/v spray solution of each by taking 11.21 mL of the herbicide concentrate, placing it into 438.80 mL of deionized water and then lightly shaking by hand until each spray sample was homogenous. The eight spray solutions were sprayed using a Teejet® 8002 flat fan nozzle (Teejet Technologies; Wheaton, Ill.) at 40 psi (276 kiloPascal) and the spray droplet size distribution measurement was performed with a Sympatec Helos/KF high resolution laser diffraction particle sizer with an R7 lens (Sympatec GmbH; Clausthal-Zellerfeld, Germany). The tip of the nozzle was situated 12 inches (30.5 centimeters) above the path of the laser beam of the Sympatec particle sizer. The percentage of driftable fines was expressed as the volume percentage of spray droplets below 150 µm volume mean diameter (VMD) as shown in Table 1.

TABLE 1

Spray Droplet Analysis of Herbicide Sprays Containing Tertiary Amine Oxide Surfactants

| Tertiary Amine Oxide Surfactant | Spray Droplet VMD, µm | Volume Percent Driftable Fines <150 µm VMD |
|---|---|---|
| none (control) | 155 | 48.1% |
| Ammonyx ® C | 206 | 31.9% |
| Ammonyx ® MO | 198 | 33.9% |
| Ammonyx ® MCO | 204 | 32.4% |
| Ammonyx ® LO | 200 | 33.5% |
| Rhodamox ® LO | 201 | 33.0% |
| Aromox ® C/12 | 235 | 23.1% |
| Ammonyx ® DO | 165 | 43.7% |

Example 2

Herbicide Concentrates

Herbicide concentrates containing 114 g ae/L 2,4-D DMA, 120 g ae/L glyphosate DMA, 30 g/L propylene glycol, and 18 g/L (dry weight basis) of the tertiary amine oxide surfactants listed in Example 1 were prepared as follows. A 100 mL volumetric flask was first charged with 20.56 g of a 55.44 wt % ae 2,4-D DMA salt solution in water. To the volumetric flask, 3.00 g of propylene glycol was added and the liquids were then blended by hand shaking the flask until the contents were homogenous. Next, 24.52 g of a 48.95 wt % ae glyphosate DMA salt solution in water were added to the flask. The volumetric flask was once again hand shaken until the contents were blended and homogenous. Next, the tertiary amine oxide surfactant was added (3.60 g of Aromox® C/12; 6.00 g for all others) and the flask was hand shaken until the contents were blended and homogenous. Lastly, deionized water was added to fill the volumetric flask to the 100 mL mark. The sample was then blended by shaking the solution by hand until the liquid was homogenous. Seven samples containing the tertiary amine oxide surfactants listed above and one concentrate containing no tertiary amine oxide surfactant (i.e., control sample) were prepared in this manner.

Each of the herbicide concentrates was then diluted in water to make a 4.99% v/v spray solution of each by taking 22.46 mL of the herbicide concentrate and placing it into 427.55 mL of deionized water and then lightly shaking by hand until each spray sample was homogenous. The eight spray solutions were sprayed using the same procedure and technique described in Example 1. The results are shown in Table 2.

TABLE 2

Spray Droplet Analysis of Herbicide Sprays Containing Tertiary Amine Oxide Surfactants

| Tertiary Amine Oxide Surfactant | Spray Droplet VMD, µm | Volume Percent Driftable Fines <150 µm VMD |
|---|---|---|
| none (control) | 150 | 50.2% |
| Ammonyx ® C | 225 | 26.9% |
| Ammonyx ® MO | 230 | 25.5% |
| Ammonyx ® MCO | 220 | 28.0% |
| Ammonyx ® LO | 198 | 34.2% |
| Rhodamox ® LO | 192 | 35.8% |
| Aromox ® C/12 | 235 | 22.3% |
| Ammonyx ® DO | 159 | 46.0% |

Example 3

Tank-Mixed Spray Solution Containing Dicamba Diglycol Ammonium (DGA) Salt, Glyphosate Isopropyl Ammonium (IPA) Salt, and a Tertiary Amine Oxide Surfactant A tank-mixed spray solution containing dicamba diglycol ammonium (DGA) salt, glyphosate isopropyl ammonium (IPA) salt, and a tertiary amine oxide surfactant was prepared. A sample container was first charged with 276.73 mL of deionized water and then 4.56 g of 30% w/w Ammonyx® LO solution was added and mixed. Next, 11.22 mL of Rodeo® herbicide concentrate (commercial 4 pounds acid equivalent per gallon (lb ae/gal) glyphosate IPA salt solution from Dow AgroSciences, LLC) and 7.49 mL of Clarity® herbicide concentrate (commercial 4 lb ae/gal dicamba DGA salt solution from BASF Corporation (Florham Park, N.J.) were added and the sample was then shaken by hand until the mixture was homogenous (<1 minute). The sample was sprayed using the same procedure and technique described in Example 1. The results, along with that for a control spray sample mixed the same way, but containing no tertiary amine oxide surfactant are shown in Table 3.

TABLE 3

Spray Droplet Analysis of a Herbicide Spray Containing Ammonyx ® LO

| Tertiary Amine Oxide Surfactant | Spray Droplet VMD, µm | Volume Percent Driftable Fines <150 µm VMD |
|---|---|---|
| none (control) | 164 | 44.7% |
| Ammonyx ® LO | 229 | 21.6% |

Example 4

Tank-Mixed Spray Solution Containing Triclopyr Triethyl Ammonium (TEA) Salt, Glyphosate Isopropyl Ammonium (IPA) Salt, and a Tertiary Amine Oxide Surfactant A tank-mixed spray solution containing triclopyr triethyl ammonium (TEA) salt, glyphosate isopropyl ammonium (IPA) salt, and a tertiary amine oxide surfactant was prepared. A sample container was first charged with 275.48 mL of deionized water and then 0.79 g of 30% w/w Ammonyx® LO solution was added and mixed. Next, 8.73 mL of Rodeo® herbicide concentrate (commercial 4 lb ae/gal glyphosate IPA salt solution from Dow AgroSciences, LLC) and 15.0 mL of Garlon 3A® herbicide concentrate (commercial 3 lb ae/gal triclopyr TEA salt solution from Dow AgroSciences, LLC) were added and the sample was then shaken by hand until the mixture was homogenous (<1 minute). The sample was sprayed using the same procedure and technique described in Example 1. The results, along with that for a control spray sample containing no tertiary amine oxide surfactant are shown in Table 4.

TABLE 4

Spray Droplet Analysis of a Herbicide Spray Containing Ammonyx ® LO

| Tertiary Amine Oxide Surfactant | Spray Droplet VMD, μm | Volume Percent Driftable Fines <150 μm VMD |
|---|---|---|
| none (control) | 158 | 47.2% |
| Ammonyx ® LO | 240 | 24.1% |

Example 5

Herbicide Concentrate Containing Armeen® DMTD dimethyltallowalkylamine

A herbicide concentrate containing 225 g ae/L of 2,4-D DMEA (dimethylethanol ammonium), 225 g ae/L of glyphosate DMA, 51 g/L of propylene glycol, and 56 g/L of Armeen® DMTD dimethyltallowalkylamine (AzkoNobel; Chicago, Ill.) was prepared as follows: 14.72 mL of a glyphosate DMA stock solution (40.5 wt % ae, density-1.208 g/mL), 14.98 mL of a 2,4-D DMEA/propylene glycol stock solution (40.3 wt % ae 2,4-D DMEA, 9.1 wt % propylene glycol, density-1.192 g/mL), and 2.25 mL (1.80 g, density-0.80 g/mL) of Armeen® DMTD were combined and swirled to yield a clear, homogeneous concentrate.

The resulting herbicide concentrate was then diluted in deionized water to make a 4% (vol/vol) spray solution in a similar manner as described in Example 1. The spray solution was sprayed using the same procedure and technique described in Example 1. The results are shown in Table 5.

TABLE 5

Spray Droplet Analysis of a Herbicide Spray Containing Armeen ® DMTD

| Tertiary Amine Surfactant | Spray Droplet VMD, μm | Volume Percent Driftable Fines <150 μm VMD |
|---|---|---|
| none (control)* | 150 | 50.2% |
| Armeen ® DMTD | 268 | 15.7% |

*The control sample was prepared using glyphosate DMA and 2,4-D DMA.

Example 6

Concentrate Containing Tomamine® AO-728 Special

A glyphosate/2,4-D concentrate formulation was prepared by blending 22.01 g of 2,4-D choline concentrate (44.30 wt % acid equivalent (ae)), 3.0 g propylene glycol, 21.22 g of glyphosate DMA concentrate (48.30 wt % ae), 3.53 g of Tomamine® AO-728 Special (50% active linear alkylpropylamine oxide, 1.77 g active; AirProducts; Allentown, Pa.), and sufficient water to charge a 50 mL volumetric flask. The formulation contained 205 g/L glyphosate DMA (ae) and 195 g/L 2,4-D choline (ae).

The resulting herbicide concentrate was then diluted in deionized water to make a 4.38% (vol/vol) spray solution in a similar manner as described in Example 1. The spray solution was sprayed using the same procedure and technique described in Example 1. The results are shown in Table 6.

TABLE 6

Spray Droplet Analysis of a Herbicide Spray Containing Tomamine ® AO-728

| Tertiary Amine Oxide Surfactant | Spray Droplet VMD, μm | Volume Percent Driftable Fines <150 μm VMD |
|---|---|---|
| none (control)* | 148 | 51.1% |
| Tomamine ® AO-728 Special | 201 | 34.0% |

*The control sample was prepared using glyphosate DMA and 2,4-D choline.

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term "comprising" and variations thereof as used herein is used synonymously with the term "including" and variations thereof and are open, non-limiting terms.

We claim:

1. A method to reduce spray drift during the application of an aqueous herbicidal spray mixture containing glyphosate and an auxinic herbicide comprising incorporating into the aqueous herbicidal spray mixture from about 0.02 to about 2 weight percent of one or more tertiary amine surfactants of the formula:

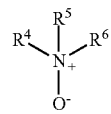

wherein $R^4$ is a straight or branched chain ($C_{10}$-$C_{18}$) alkyl or an alkyletherpropyl or alkylamidopropyl of the formula:

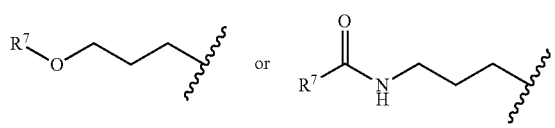

wherein $R^7$ is a straight or branched chain ($C_{10}$-$C_{18}$) alkyl, and $R^5$ and $R^6$ independently are straight or branched chain ($C_1$-$C_{18}$) alkyl or ethoxylates or propoxylates of the formula:

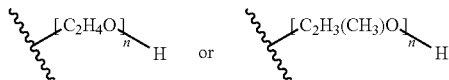

or 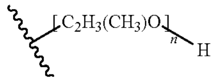 wherein n is an integer from 1 to 20, or mixtures thereof.

2. The method of claim 1, wherein the auxinic herbicide is 2,4-D choline salt.

3. The method of claim 1, wherein the auxinic herbicide is 2,4-D dimethyl ammonium salt.

4. The method of claim 1, wherein the auxinic herbicide is 2,4-D choline salt or 2,4-D dimethyl ammonium salt and the glyphosate is glyphosate dimethyl ammonium salt or glyphosate isopropyl ammonium salt.

5. The method of claim 1, wherein the tertiary amine oxide surfactant is lauryldimethylamine oxide.

6. The method of claim 1, wherein the auxinic herbicide is 2,4-D choline salt or 2,4-D dimethyl ammonium salt, the glyphosate is glyphosate dimethyl ammonium salt or glyphosate isopropyl ammonium salt, and the tertiary amine oxide surfactant is a lauryldimethylamine oxide.

7. The method of claim 1, wherein the auxinic herbicide is 2,4-D choline salt, the glyphosate is glyphosate dimethyl ammonium salt, and the tertiary amine oxide surfactant is a lauryldimethylamine oxide.

8. The method of claim 1, wherein the median diameter of a plurality of the spray droplets created is increased above that of a composition that does not include the tertiary amine oxide surfactant.

9. The method of claim 1, wherein the production of fine spray droplets smaller than 150 μm in diameter is decreased below that of a composition that does not include the tertiary amine oxide surfactant.

10. The method of claim 1, wherein the aqueous herbicidal spray mixture is homogeneous and free-flowing at temperatures between 54° C. and about −10° C.

11. The method of claim 1, wherein the auxin herbicide is a water soluble salt of 2,4-D and the ratio of the water-soluble salt of 2,4-D to glyphosate is from about 2.3:1 to about 1:2.3.

* * * * *